(12) United States Patent
Auksorius et al.

(10) Patent No.: US 10,743,767 B2
(45) Date of Patent: Aug. 18, 2020

(54) FULL-FIELD INTERFERENTIAL IMAGING SYSTEMS AND METHODS

(71) Applicant: CENTRE NATIONAL DE LA RECHERCHE SCIENTIFIQUE, Paris (FR)

(72) Inventors: Egidijus Auksorius, Paris (FR); Albert Claude Boccara, Paris (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/320,982

(22) PCT Filed: Jul. 25, 2017

(86) PCT No.: PCT/EP2017/068717
§ 371 (c)(1),
(2) Date: Jan. 25, 2019

(87) PCT Pub. No.: WO2018/019808
PCT Pub. Date: Feb. 1, 2018

(65) Prior Publication Data
US 2019/0167109 A1    Jun. 6, 2019

(30) Foreign Application Priority Data

Jul. 26, 2016    (FR) ..................................... 16 57173

(51) Int. Cl.
*G01B 9/02*    (2006.01)
*A61B 5/00*    (2006.01)
(Continued)

(52) U.S. Cl.
CPC ............ *A61B 5/0066* (2013.01); *A61B 5/441* (2013.01); *G01B 9/02015* (2013.01);
(Continued)

(58) Field of Classification Search
CPC ............ G01B 9/02015; G01B 9/02049; G01B 9/0209; G01B 9/20291; G01N 21/47
See application file for complete search history.

(56) References Cited

U.S. PATENT DOCUMENTS

2006/0114411 A1    6/2006  Wei et al.
2010/0157308 A1    6/2010  Xie
(Continued)

FOREIGN PATENT DOCUMENTS

DE    10 2007 054 283 A1    5/2009
JP         62-186841 A        8/1987

OTHER PUBLICATIONS

Auksorius, et al., "Dark-field full-field optical coherence tomography", Optics Letters, vol. 40, No. 14, Jul. 15, 2015.
(Continued)

*Primary Examiner* — Jonathan M Hansen
(74) *Attorney, Agent, or Firm* — Baker & Hostetler LLP (57) ABSTRACT

A system for the full-field interferential imaging of a sample, includes an illumination path with a light source, an interferometer with at least one first objective, and a separating element for receiving incident light waves via an input face and for forming an object arm for receiving the sample and a reference arm on which a reflection device is arranged, the reflection device being used to reflect incident light waves in a direction different from the direction of incidence. The separator element has a reflection coefficient and a transmission coefficient that are non-equal such that the proportion of the optical power of the incident light waves sent to the object arm is strictly larger than the proportion of the optical power of the light waves sent to the reference arm. The system also comprises a detection path comprising a two-dimensional image acquisition device, the illumination path and the detection path comprising a common path (Continued)

comprising\input face of the separator element and being separated by a reflection element.

10 Claims, 8 Drawing Sheets

(51) Int. Cl.
*G02B 27/14* (2006.01)
*G02B 27/10* (2006.01)
*G01N 21/47* (2006.01)
*G06K 9/00* (2006.01)

(52) U.S. Cl.
CPC ......... *G01B 9/02091* (2013.01); *G01N 21/47* (2013.01); *G02B 27/108* (2013.01); *G02B 27/143* (2013.01); *G06K 9/0004* (2013.01); *G01N 2021/4709* (2013.01)

(56) References Cited

U.S. PATENT DOCUMENTS

| 2013/0010302 A1 | 1/2013 | Sharma et al. |
| 2013/0235383 A1 | 9/2013 | Boccara et al. |
| 2014/0111772 A1 | 4/2014 | Ikegami |
| 2016/0113507 A1* | 4/2016 | Reza .................. G01N 21/1717 |

OTHER PUBLICATIONS

Watanabe, et al., "In vivo non-mechanical scanning grating-generated optical coherence tomography using an InGaAs digital camera", Optics Communications, Optics Communications, vol. 261, Issue 2, pp. 376-380, May 15, 2006.

Auksorius, et al., "Fingerprint imaging from the inside of a finger with full-field optical coherence tomography", Biomedical Optics Express, vol. 6, Issue 11, pp. 4465-4471, Nov. 1, 2015.

* cited by examiner

PRIOR ART

PRIOR ART

FULL-FIELD INTERFERENTIAL IMAGING SYSTEMS AND METHODS

CROSS-REFERENCE TO RELATED APPLICATIONS

This application is a National Stage of International patent application PCT/EP2017/068717, filed on Jul. 25, 2017, which claims priority to foreign French patent application No. FR 1657173, filed on Jul. 26, 2016, the disclosures of which are incorporated by reference in their entirety.

FIELD OF THE INVENTION

The present description relates to full-field optical-coherence-tomography imaging methods and systems. In particular it applies to the acquisition of fingerprints and to imaging of the skin.

BACKGROUND

Techniques for acquiring images by full-field optical-coherence-tomography (OCT) imaging with incoherent light are described for interference-microscopy applications and are very effective non-invasive and non-destructive methods for acquiring images at depth in biological tissues.

A full-field interference-microscopy technique is for example described in the article "Full-field optical coherence tomography" by A. Dubois a C. Boccara, extracted from the work "Optical Coherence Tomography—Technology and Applications"—Wolfgang Drexler—James G. Fujimoto—Editors—Springer 2009, the experimental setup of which is reproduced in FIG. 1A.

Figure 1A:
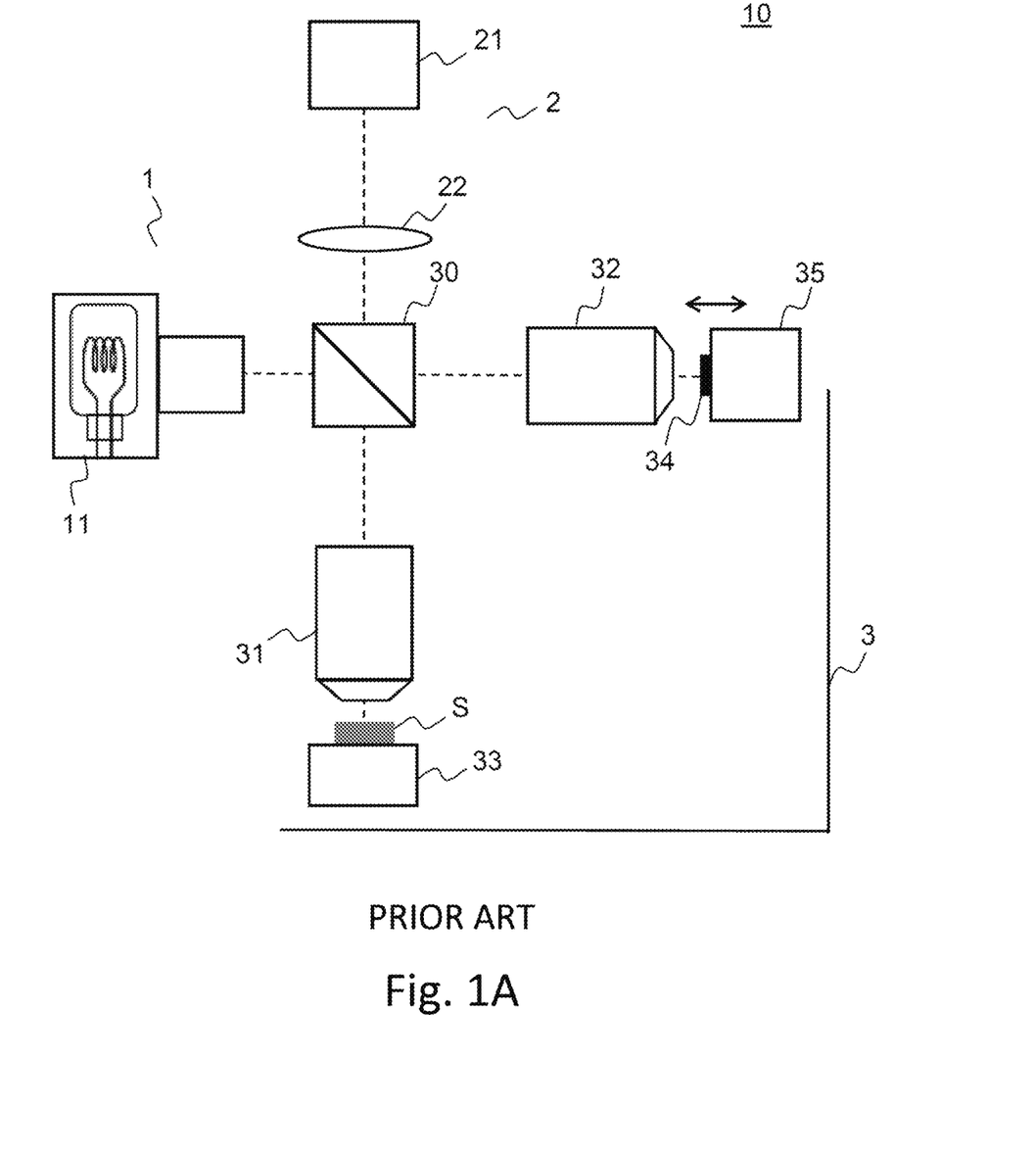
FIG. 1A (already described) illustrates a first full-field interference-microscopy system according to the prior art.

The interference-microscopy system 10 known from the prior art and reproduced in FIG. 1A in particular comprises an illumination channel 1 with a low-coherence light source 11, and a detection channel 2 with a camera 21 and a lens 22 (so-called tube lens) allowing a plane of the sample S that it is desired to image and a detection plane of the camera to be optically conjugated. The system 10 moreover comprises an interferometer 3—in this example a Linnik device—comprising a splitting element 30 suitable for receiving the light waves emitted by the source 11 and for sending them to an object arm in which the sample S is arranged and a reference arm in which a reference mirror 34 is arranged, respectively. In each of the object and reference arms are positioned identical microscope objectives, referenced 31 and 32 in FIG. 1A, respectively. Axial moving devices 33, 35, for example piezoelectric motors, allow the sample S and the reference mirror 34 to be moved along the optical axis of the microscope objective 31 and along the optical axis of the microscope objective 32, respectively. In practice, the sample S, for example a sample of biological tissue, may be applied against a silica window that ensures the planarity of its surface and thus avoids aberrations that topographical irregularities in the surface of the sample could induce. To decrease the parasitic signal of reflection from the surface of the window, an antireflection treatment may be deposited thereon or an immersion objective with a coupling liquid that possesses a refractive index similar to that of silica may be used.

The full-field OCT imaging technique is based on the exploitation of light backscattered by the sample when it is illuminated by a light source of small coherence length, and in particular the exploitation of light backscattered by cellular and tissular microscopic structures in the case of a biological sample. This technique exploits the low temporal coherence of the light source to isolate the light backscattered by a virtual slice located at depth in the sample. The use of an interferometer allows an interference signal representative of the light selectively originating from a given slice of the sample to be generated, via interference between the light waves backscattered by the sample and the light waves reflected by the reference mirror, and light originating from the rest of the sample to be eliminated. This technique allows three-dimensional images with a typical resolution of about 1 μm to be obtained.

Very recently, E. Auksorius et al. ("*Dark-field full-field optical coherence tomography*", Optics Letters, Vol. 40, No. 14 (2015)) have shown how the contrast of the images may be clearly improved, in a full-field interference-microscopy system of the type shown in FIG. 1A, by virtue of suppression of the specular reflections from the air/glass interfaces formed by the windows of the elements for holding the sample in particular.

Figure 1B:
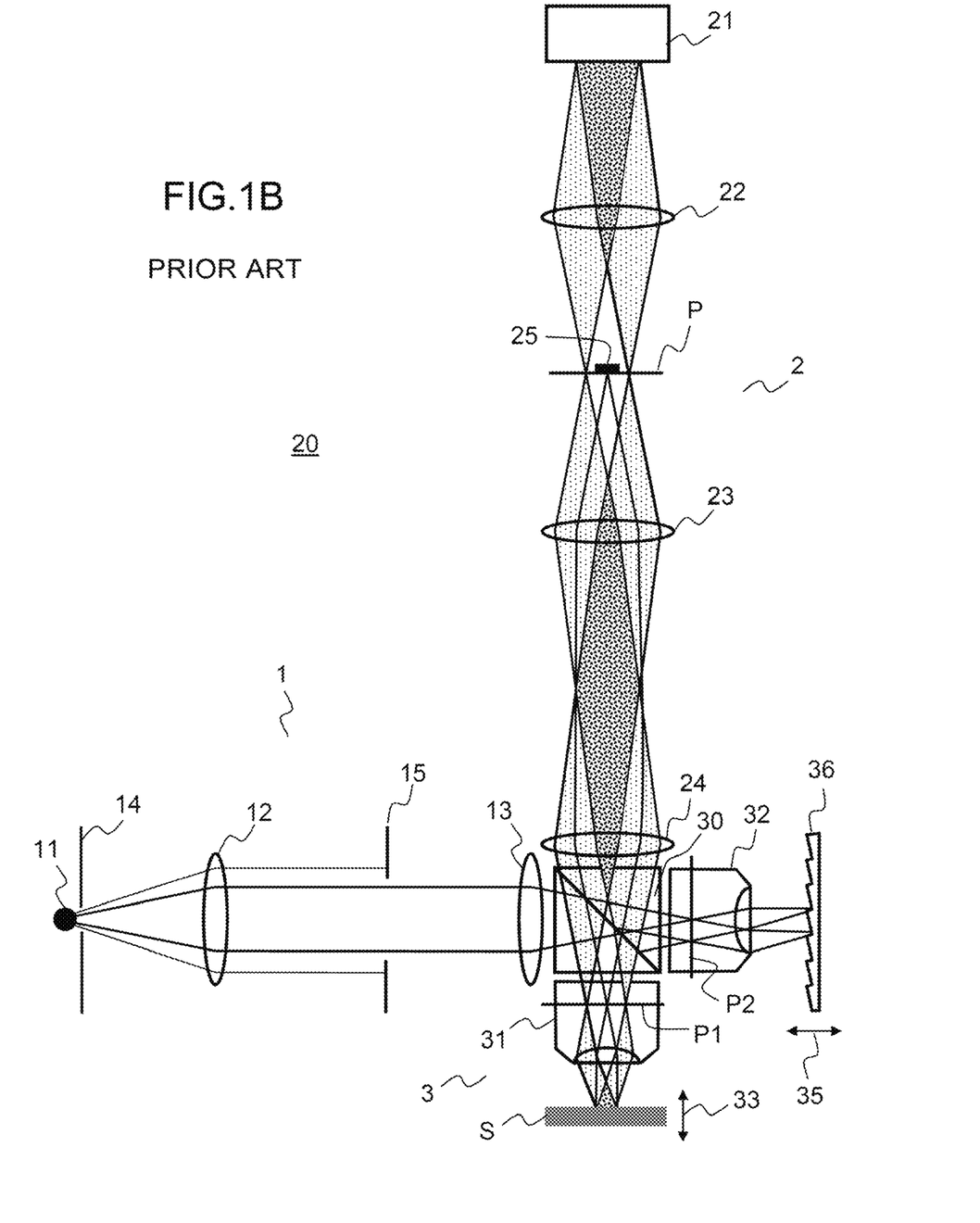
FIG. 1B (already described) illustrates a second full-field interference-microscopy system according to the prior art.

FIG. 1B shows a schematic of the experimental setup described in the article by E. Auksorius et al. cited above. The interference-microscopy system 20 shown in FIG. 1B comprises, just like that shown in FIG. 1A, an illumination channel 1, a detection channel 2 and an interferometer 3. The interferometer 3 comprises, in each of the object and reference arms formed by means of the splitting element 30, a microscope objective, referenced 31 and 32, respectively. The illumination channel comprises, in addition to the light source 11, an optical system 12, 13 for imaging the source 11 in an image focal plane of the microscope objectives. The image focal planes of the microscope objectives 31, 32 are coincident with the pupillary planes P1, P2 of the microscope objectives 31 and 32, respectively. An aperture diaphragm arranged in a plane 14 that is substantially coincident with that of the source 11 allows the spatial extent of the source to be adjusted and a field diaphragm arranged in a plane 15 that is conjugate with the reference mirror allows the field of view on the sample to be adjusted. The detection channel 2 comprises, in addition to the camera 21 and to the tube lens 22, an optical relay system 23, 24, allowing a pupillary plane P that is conjugate with the pupillary planes P1, P2 to be formed. The suppression of the specular reflections is obtained by means of an opaque disc 25 positioned in the detection channel, in the conjugate plane P of the pupillary planes P1, P2. Moreover, the reference mirror in the reference arm has been replaced by a blazed grating 36 such that the zeroth order is blocked by the opaque disc, the optical interference occurring between the 1st order (dominant via the blaze effect) diffracted by the grating and the light backscattered by the sample, which is only partially blocked by the opaque disc. The dimensions of the aperture diaphragm in the plane 14 are adjusted such that the dimensions of the image of the aperture diaphragm in the plane of the opaque disc 25 are smaller than those of the opaque disc 25; thus, all of the specular reflections issued from the interferometer are blocked. Such a system makes it possible to do without antireflection treatments on the windows of the elements for holding the samples, in particular when it is not possible to work with immersion microscope objectives.

Whatever the full-field OCT imaging system used, the sensitivity of the system is however limited by the amount of light coming from the sample that may be detected by the camera. Specifically, if R is the reflection coefficient of the splitting element 30 and T its transmission coefficient, and if it is assumed that the splitting element is optically lossless (R=1−T), the maximum amount of light coming from the sample that it is possible to collect is equal to R×T=T(1−T)

and has an optimum for R=T=0.5, this corresponding to a maximum amount of light coming from the sample equal to 25% of the amount of light emitted by the source.

One possible way of collecting a higher light flux coming from the sample would be to increase the light intensity of the source, but this is not always possible in particular because of limitations on the photon budget of the sources used and because of the photosensitivity of certain samples. Another one way would be to duplicate the detection channel in order to collect both the flux reflected and the flux transmitted by the splitting element, but this would require two cameras.

The present description proposes an original architecture for a full-field OCT imaging system that allows, with respect to known prior-art systems, the amount of light coming from the sample that may be detected by the camera to be increased, without however increasing the light flux incident on the sample or the number of cameras. Such a full-field OCT imaging system is particularly suitable for low-cost systems for applications such as the acquisition of fingerprints and imaging of the skin.

SUMMARY OF THE INVENTION

According to a first aspect, the present description relates to a full-field optical-coherence-tomography system for imaging a sample, generally comprising an illumination channel comprising a light source for emitting incident light waves, an interferometer, a detection channel comprising a device for acquiring two-dimensional images and a processing unit.

The interferometer of the imaging system according to the first aspect comprises at least one first objective, the light source being arranged in proximity to an image focal plane of the first objective or in proximity to a plane that is conjugate with an image focal plane of the first objective and a splitting element suitable for receiving, via an entrance face, the incident light waves and suitable for forming an object arm intended to receive the sample and a reference arm in which is arranged a reflecting device. The splitting element has a reflection coefficient and a transmission coefficient that are not equal, such that the proportion of the optical power of the incident light waves sent to the object arm is strictly higher than the proportion of the optical power of the light waves sent to the reference arm. The reflecting device in the object arm is suitable for directing the incident light waves in a direction that is different from the direction of incidence.

Moreover, the interferometer of the imaging system according to the first aspect is suitable for producing, when the sample is placed in the object arm of the interferometer, at each point of an imaging field, interference between a reference wave obtained by reflection of incident light waves from an elementary surface of the reflecting device corresponding to said point of the imaging field and an object wave obtained by backscatter of incident light waves by a voxel of a slice of the sample at a given depth, said voxel corresponding to said point of the imaging field.

The device for acquiring two-dimensional images is positioned in a conjugate plane of the reflecting device and suitable for acquiring two-dimensional interferometric signals resulting from the interference produced at each point of the imaging field.

The illumination channel and the detection channel comprise a common channel comprising said entrance face of the splitting element, and are separated by a reflecting element, which is positioned in proximity to an image focal plane of said first objective, or in proximity to a conjugate plane of said image focal plane of the first objective, said reflecting element being suitable for letting pass, in the detection channel, at least one portion of the light waves directed by the reflecting device of the reference arm and for letting pass, in the illumination channel, at least one portion of the incident light waves.

The processing unit is configured to calculate an image of the sample from said two-dimensional interferometric signals.

The applicants have shown that this original architecture of a full-field optical-coherence-tomography imaging system allows, with respect to known prior-art systems, the optical power backscattered by the sample and which may be detected by the camera to be increased, without however increasing the optical power incident on the sample or the number of cameras.

According to one or more example embodiments, the reflection coefficient and the transmission coefficient of the splitting element are such that at least 90% of the optical power of the light waves incident on the splitting element are sent toward the object arm. The applicants have shown that with such a configuration, the optical power backscattered by the sample and which may be detected by the camera is increased by more than a factor of 3 with respect to known prior-art systems.

According to one or more example embodiments, the reflecting element comprises a mirror that is inclined with respect to the optical axis of the first objective, which is apertured for the passage of the incident light waves, the dimensions of the aperture being sufficiently small to not block all of the light waves directed into the detection channel.

According to one or more example embodiments, the reflecting element comprises a mirror that is inclined with respect to the optical axis of the first objective in order to deflect toward the common channel the incident light waves, and that has dimensions that are sufficiently small to not block all of the waves directed into the detection channel.

In one or more of these example embodiments, in the case of a spatially incoherent light source, of given geometric extent, the maximum dimension of the aperture—or of the inclined mirror—will possibly be chosen to be smaller than or substantially equal to the maximum dimension of the geometric extent of the image of the source on the mirror.

According to one or more example embodiments, the reflecting device of the reference arm comprises a reflective diffraction grating, for example a blazed grating.

According to one or more example embodiments, the reflecting device of the reference arm comprises an inclined mirror.

According to one or more example embodiments, the interferometer is a Michelson interferometer, said first objective being arranged in the common channel of the illumination and detection channels.

According to one or more example embodiments, the interferometer is a Linnik interferometer and comprises said first objective in the reference arm of the interferometer, and a second objective in the object arm of the interferometer.

According to one or more example embodiments, said objectives are microscope objectives.

According to a second aspect, the present description comprises a full-field optical-coherence-tomography method for imaging a sample by means of an imaging system according to the first aspect.

The method comprises, according to one or more example embodiments:

placing the sample in the object arm of the interferometer;

producing, by means of said interferometer, for each point of an imaging field, interference between a reference wave obtained by reflection of incident light waves from the reflecting device of the reference arm of the interferometer, said elementary surface corresponding to said point of the imaging field, and an object wave obtained by backscatter of the incident wave by a voxel of a slice of the sample at a given depth, said voxel corresponding to said point of the imaging field;

acquiring, for at least one value of the optical path difference between the object arm and the reference arm, at least one two-dimensional interferometric signal resulting from interference for each point of the imaging field;

calculating an image of the sample from said two-dimensional interferometric signals.

The advantages mentioned with respect to the imaging system are transposable to the imaging method according to the second aspect of the present description.

The various embodiments of the imaging method according to the second aspect of the present description are combinable together.

Various features and embodiments of the various aspects of the present description may also be combined together.

BRIEF DESCRIPTION OF THE DRAWINGS

Other advantages and features of the imaging technique presented above will become apparent on reading the following detailed description, which is given with reference to the figures, in which.

DETAILED DESCRIPTION

Figure 2A:
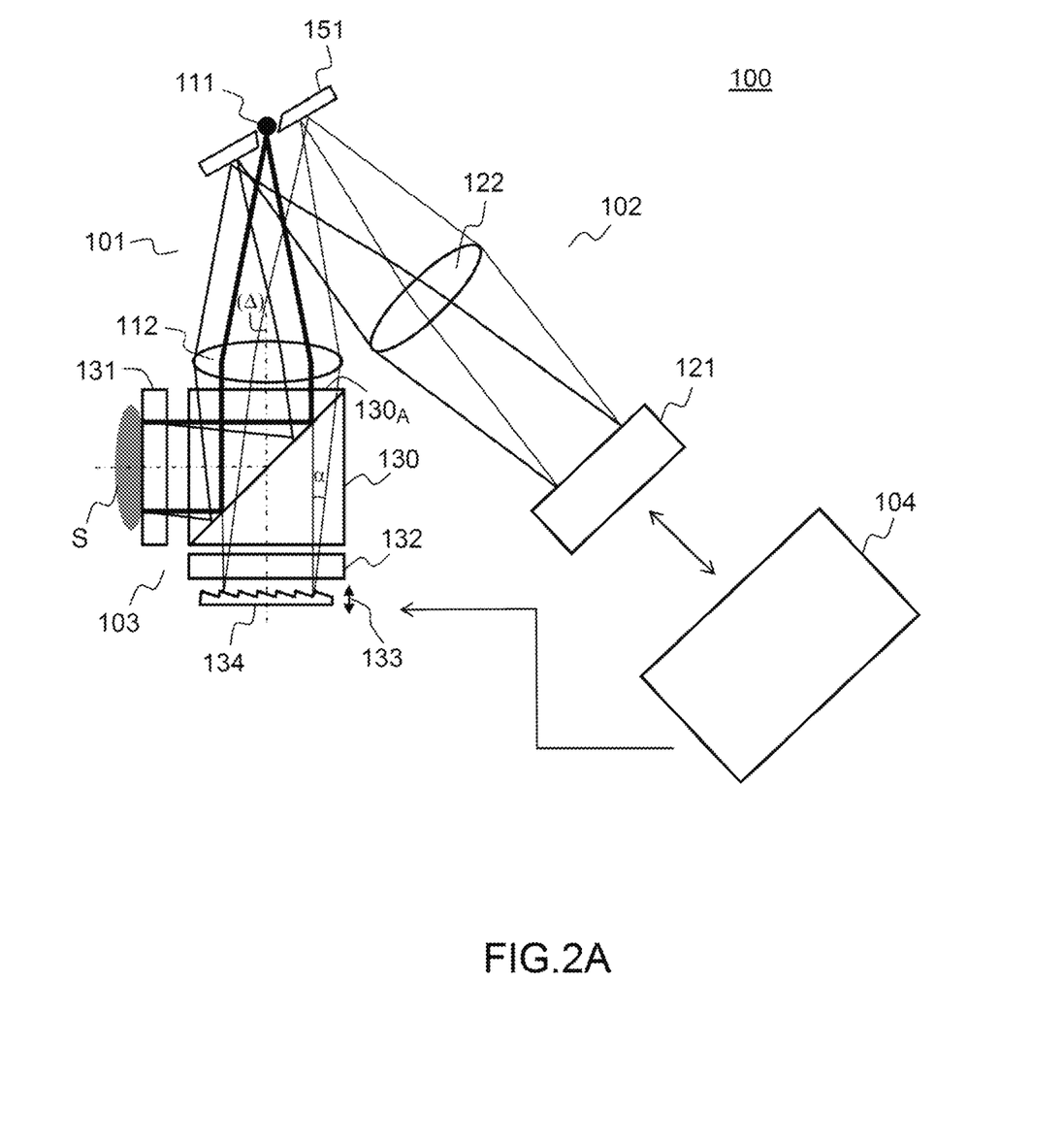
FIGS. 2A and 2B show schematic diagrams of example embodiments of a full-field optical-coherence-tomography imaging system according to a first embodiment of the present description.
Figure 2B:
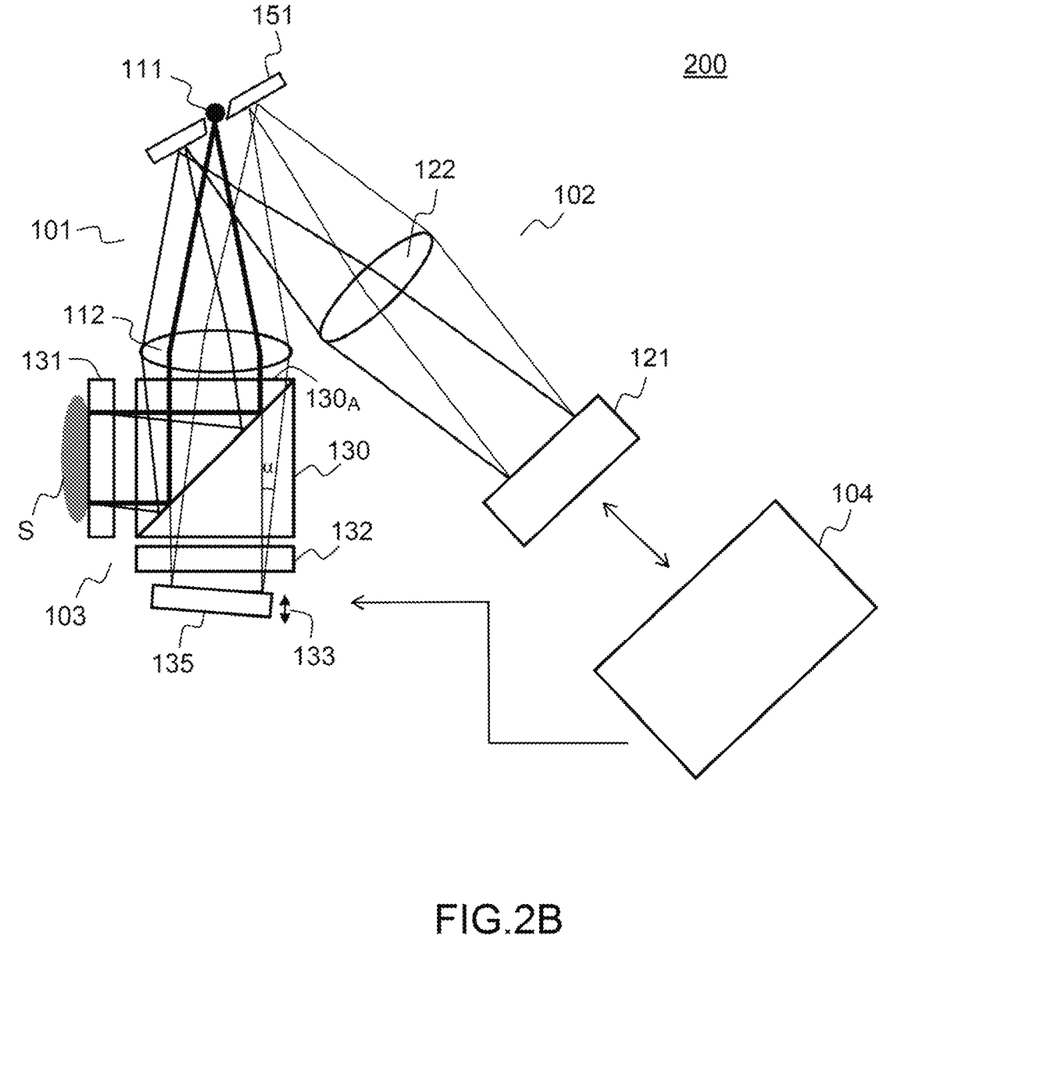

Two examples of optical-coherence-tomography (OCT) imaging systems 100, 200 suitable for implementing methods for imaging a sample S according to the present description are schematically shown in FIGS. 2A and 2B.

In each of these examples, the OCT imaging system comprises an illumination channel 101, in particular with a light source 111 for emitting incident light waves, a detection channel 102, in particular comprising a device 121 for acquiring two-dimensional images, and an interferometer 103 comprising at least one first objective, in this example an objective referenced 112, and a splitting element 130 suitable for receiving, via an entrance face 130A the incident light waves. The splitting element 130 is suitable for forming an object arm that is intended to receive the sample S for which it is desired to produce an image, for example a tomographic image at a given depth, and a reference arm in which is arranged a reflecting device (134 in FIG. 2A and 135 in FIG. 2B). In the reference arm, the reflecting device may be mounted on an axial moving device symbolized by a double arrow 133, for example a piezoelectric motor, a stepper motor or a combination of both thereof. The axial moving device allows the reflecting device to be moved axially, i.e. to be moved along the optical axis defined by the optical axis A of the objective 112 and represented by a dot-dashed line in FIG. 2A, and in particular allows the optical path difference between the object arm and the reference arm to be modified. In the object arm, the sample S is for example applied against a window 131 that is transparent to the incident light waves, for example a window made of silica. The sample S may, according to one or more example embodiments, also be mounted on an axial moving device (not shown in FIGS. 2A and 2B), for example a piezoelectric motor, a stepper motor or a combination of both thereof in order to ensure an axial movement of the sample and to adjust a depth at which it is desired to form an image. Alternatively, the axial moving device 133 for moving the reflecting device axially may perform this function. The OCT imaging system furthermore comprises a processing unit 104 connected on the one hand to the device 121 for acquiring two-dimensional images and on the other hand to the movable device(s).

According to one example embodiment, the interferometer 103 is suitable for producing optical interference between, on the one hand, reference waves obtained by reflection of the light emitted by the light source 111 by each elementary surface of the surface of the reflecting device 134, 135 of the reference arm of the interferometer and, on the other hand, object waves obtained by backscatter of the light emitted by the same source by each voxel of a slice of the sample S located at depth in the sample, the sample S being placed in the object arm of the interferometer, said voxel and said elementary surface corresponding to the same point of the imaging field.

The light source 111 is according to one or more example embodiments a temporally incoherent source or a source of small temporal coherence length (advantageously having a coherence length comprised between 1 and 100 µm). It is for example a halogen lamp or a light-emitting diode (LED).

The acquiring device 121 allows at least one two-dimensional interferometric signal resulting from interference between the reference waves and the object waves to be acquired. The acquiring device 121 is for example an image sensor, such as a charge-coupled-device (CCD) or complementary metal-oxide-semiconductor (CMOS) camera. Such an acquiring device is capable of acquiring images at a high rate, for example at a frequency higher than a few hundred Hz, or even higher than 1 kHz.

The processing unit 104 is configured to execute at least one step of processing the at least one two-dimensional interferometric signal acquired by the acquiring device 121 and/or at least one step of generating images according to at least one of the imaging methods according to the present description, in order to generate at least one image of the slice of the sample S.

In one embodiment, the processing unit 104 is a computational device comprising a first memory CM1 (not shown) for storing digital images, a second memory CM2 (not shown) for storing program instructions and a data processor, which is able to execute the program instructions stored in this second memory CM2, in particular in order to control the execution of at least one step of processing at least one two-dimensional interferometric signal acquired by the acquiring device 121 and/or at least one step of calculating images according to at least one of the imaging methods according to the present description. The processing unit may also take the form of an integrated circuit, comprising electronic components suitable for implementing the one or more functions described in this document with respect to the processing unit. The processing unit 104 may also be implemented by one or more physically separate devices.

The interferometer 103 shown in FIGS. 2A and 2B is a Michelson interferometer and comprises an objective 112, the light source 111 being arranged in proximity to an image focal plane of the objective 112. Thus, the incident light waves emitted by the source 111 and output from the objective 112 are substantially collimated when they strike the entrance face 130A of the splitting element 130. According to one or more embodiments, the light source 111 may be arranged in proximity to a plane that is conjugate with an image focal plane of the objective 112, in which case the illumination channel comprises an optical system for conveying the image of the source to the image focal plane of the objective.

As illustrated in FIGS. 2A and 2B, the splitting element 130 has a reflection coefficient and a transmission coefficient that are not equal, such that the optical power of the incident light waves (more simply called "incident optical power" in the rest of the description) sent to the object arm is strictly higher than the optical power of the incident light waves sent to the reference arm. In the examples of FIGS. 2A and 2B, the reflection coefficient for the incident light waves is strictly higher than the transmission coefficient such that a larger portion of the optical power incident on the entrance face is reflected toward the object arm in which the sample S is located. Alternatively, the transmission coefficient may be strictly higher than the reflection coefficient, in which case, in FIGS. 2A and 2B, the positions of the object and reference arms would be inverted.

According to one or more example embodiments, the reflection coefficient and the transmission coefficient of the splitting element are such that at least 75% and advantageously at least 90% of the optical power incident on the splitting element is sent to the object arm.

Thus, as illustrated in FIGS. 2A and 2B, the detection channel 102 comprises, with the illumination channel 101, a common channel that comprises, in addition to the object and reference arms, said entrance face 130A of the splitting element 130. The detection and illumination channels are separated by a reflecting element 151 that is positioned in proximity to an image focal plane of the objective 112 or in proximity to a plane that is conjugate with the image focal plane of the objective 112. In the examples of FIGS. 2A and 2B, the reflecting element is positioned in a plane that is substantially coincident with the plane of the emitting source 111.

More precisely, in these examples, the reflecting element 151 is an apertured mirror that allows, in the detection channel, at least one portion of the light waves directed by the reflecting device of the reference arm to be let past and, in the illumination channel, at least one portion of the light waves emitted by the emitting source 111 to be let past. To do this, the reflecting device of the reference arm is suitable for directing the incident light waves in a direction that is different from the direction of incidence of the incident waves, as will be described in more detail below. Thus, in this example, the light waves emitted by the emitting source 111 pass through the aperture whereas the waves reflected by the reflecting device of the reference arm are directed toward the acquiring device 121 of the detection channel.

According to one or more example embodiments, the light source 111 has a low temporal coherence but is spatially coherent. For example, the light source 111 is a super-luminescent diode, a mode-locked titanium-sapphire laser, a supercontinuum fiber laser (i.e. one based on the generation of a supercontinuum in a non-linear fiber, for example a photonic-crystal fiber). In this case, the focal spot of the incident light waves being very small, the aperture in the mirror 151 may be very small, typically of maximum transverse dimension (for example the dimension of the diameter in the case of a round aperture) comprised between 5 µm and 100 µm, and the loss of the backscattered signal due to the aperture negligible. However, spatially coherent sources run the risk of introducing crosstalk.

According to one or more example embodiments, the light source 111 has a low temporal coherence and is spatially incoherent. It is for example a light-emitting diode (LED), a halogen lamp, or an arc lamp. Cross-talk effects are therefore avoided. In this case, the aperture of the apertured mirror 151 is dimensioned to cover the largest possible geometric extent of the source—in order to benefit from the highest possible optical power of the source—without losing too much of the backscattered flux. Thus typically, it is possible to choose as maximum dimension for the aperture (diameter for example), a dimension smaller than or substantially equal to the maximum dimension of the geometric extent of the source level with the aperture, for example a dimension comprised between 1 mm and 5 mm depending on the spatial extent of the source. For example, an LED generally has an emitting area of 1 mm×1 mm size. However, the light waves emitted are very divergent and it may be necessary to increase the emitting area, for example to 4 mm×4 mm, in order to decrease the divergence, so that all the light can be collected by the objective 112. An aperture of corresponding dimensions, for example a circular aperture of diameter of about 4 mm, will then possibly be chosen.

The use of a splitting element 130 with a reflection coefficient and a transmission coefficient that are different makes it possible to exceed, by virtue of the arrangement of the illumination and detection channels described above, the maximum amount coming from the sample equal to 25% of the amount of light emitted by the source, identified in the prior art.

Specifically, if R is the reflection coefficient of the splitting element 130 and T its transmission coefficient, and if it is assumed that the splitting element is optically lossless, the maximum luminous power originating from the sample that it is possible to collect is now equal to R×R in the object arm and T×T in the reference arm, assuming the case where R>T (as in FIGS. 2A and 2B). Thus, for example, if R=90% and T=10%, and if it is assumed that the reflecting device 134 reflects 100% of the incident light, it follows that 1% of the light will be transmitted after the double passage through the splitting element in the reference arm. This is a proportion of light that is optimal for the imaging of most biological tissues, because it is sought to have substantially the same amount of light reflected by the reflecting device and by the sample. If it is assumed that the sample S reflects 100% of the incident light, it follows that the maximum optical power coming from the sample that it is possible to collect is more than 3 times higher than the optical power, i.e. the amount of light, that is obtained with a 50/50 splitting element such as described in the prior art.

In the example of FIG. 2A, the reflecting device 134 is a reflective diffraction grating, for example a blazed grating, the optical interference forming between the 1st order (dominant via the blaze effect) diffracted by the grating, and the light backscattered by the sample.

To dimension the grating, firstly the angle α that allows the light diffracted by the grating to be directed away from the aperture is determined. If f is the focal length of the objective 112 and D is the diameter of the aperture in the apertured mirror 151, the angle α respects:

$$\alpha = \text{Arctan}(D/f) \quad (1)$$

Next a grating that allows the incident waves to be diffracted with the angle α is chosen. It is possible for example to use the grating formula:

$$d = \lambda/\sin(\alpha) \quad (2)$$

where d is the distance between two lines of the grating and λ is the wavelength.

Thus, for example, for a focal length f=100 mm, and a diameter D=4 mm, a=2.3° is calculated. It is possible to deduce therefrom d=λ/sin(α)≈λ×f/D=0.85 μm×100 mm/4 mm=21.25 μm, or, in terms of line density, 47 lines per millimeter (lpm).

Reflecting devices other than a diffraction grating are possible.

Thus, in the example of FIG. 2B, the reflecting device 135 comprises a single inclined mirror, which is also suitable for directing the incident light waves in a direction that is different from the direction of incidence of the incident waves. In this case, the inclination of the mirror 135 must be chosen in the same way so that the waves reflected by the mirror are not directed into the aperture. To this end, a mirror inclined with an angle equal to a/2 with respect to the optical axis of the objective 112 will for example be chosen.

In practice, in OCT imaging systems according to the present description, it will possibly be preferred to use a diffraction grating or an inclined mirror as reflecting device, for the reasons explained with reference to FIGS. 3A and 3B.

Figure 3A:
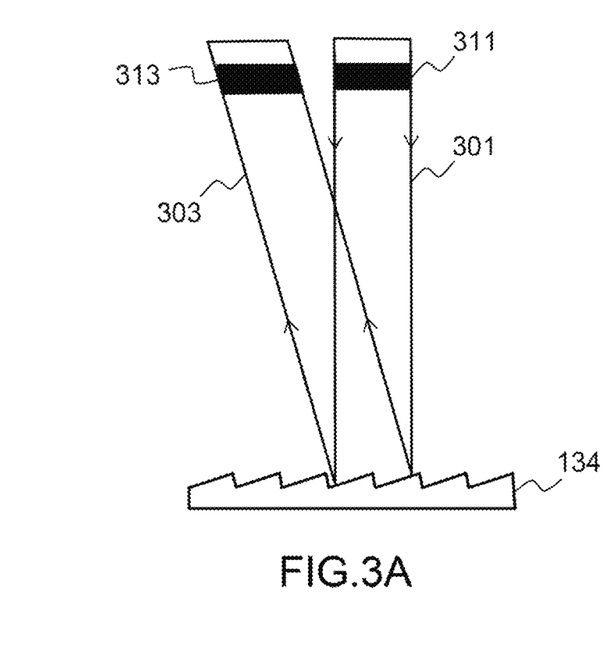
FIGS. 3A and 3B illustrate, via schematics, the reflection of a light wave from a grating-type reflecting device (FIG. 3A) and from a mirror-type reflecting device (FIG. 3B)
Figure 3B:
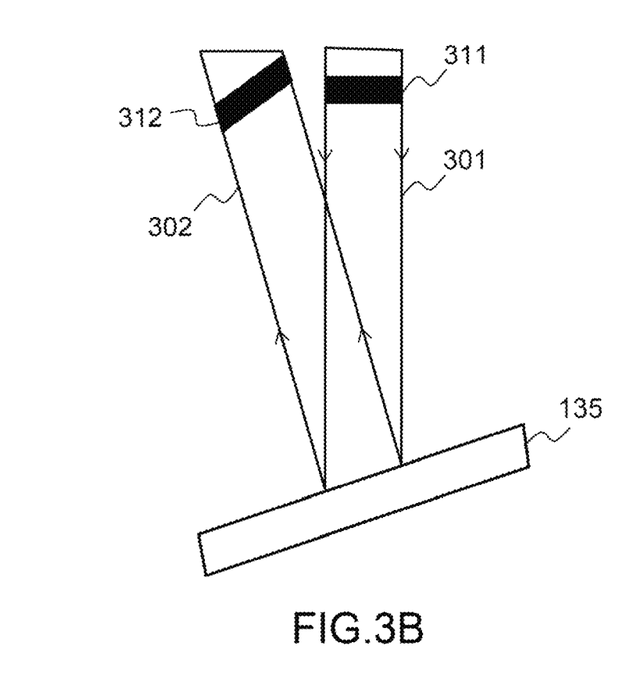

The diffraction grating may for example be used in the case where en-face images of a sample are desired; specifically, as illustrated in FIG. 3A, the orientation of the coherence slice 313 of the beam 303 that is diffracted by the grating 134 will be the same as the orientation of the coherence slice 311 of the beam 301 incident on the grating. As the light backscattered by the sample also preserves its coherence slice parallel to the incident beam, it will interfere with the reference beam en face—everywhere in the field of vision—and therefore, will produce an en-face image. For example, en-face imaging is preferred in the imaging of fingerprints since internal fingerprints have this orientation.

In the case of the use of an inclined mirror (135, FIG. 3B), the coherence slice 312 of the reflected beam is inclined with respect to the coherence slice 311 of the incident beam 301. Thus, when such a reference beam interferes with the beams backscattered by a sample, an image is generated at a nonzero angle with respect to the en-face situation described above. This imaging mode may be used when it is desired to acquire images with a cross section that is inclined with respect to the surface or when various layers oriented parallel to the surface must be captured in a single image.

In the example of FIGS. 2A and 2B, an optic 122, called in the rest of the description the "intermediate lens", for example an achromatic doublet, is placed in the detection channel 102, this intermediate optic allowing the focal object plane of the objective 112 and the detection plane of the acquiring device 121 to be conjugated, with a view to allowing interference signals produced by the interferometer to be acquired by the acquiring device. The focal length of the intermediate lens is selected to allow suitable sampling of the sample S by the acquiring device 121. The focal length of the optic 122 is for example comprised between 30 mm and 300 mm, and for example about one-hundred millimeters.

Figure 4:
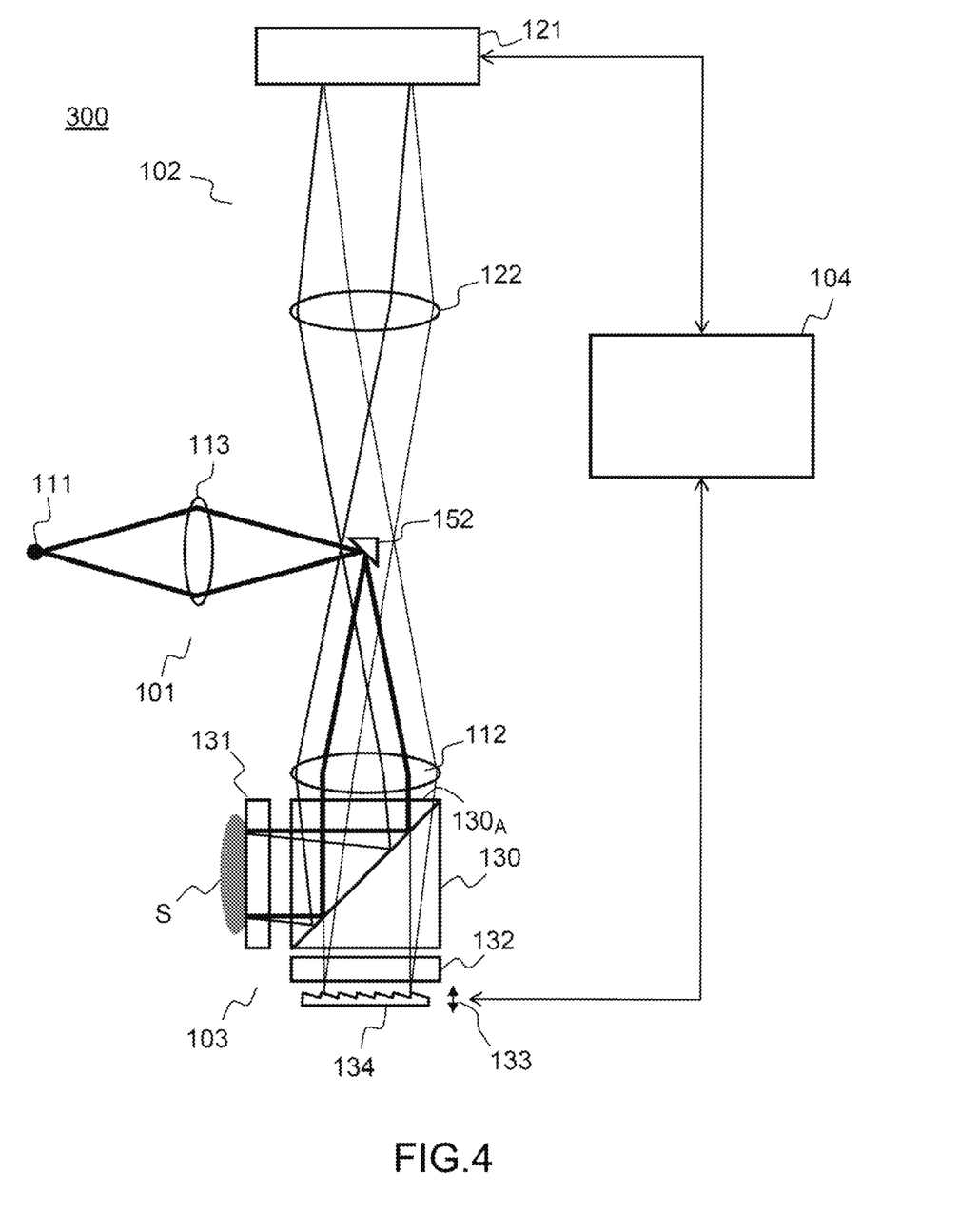
FIGS. 4 and 5 show schematic diagrams of example embodiments of a full-field optical-coherence-tomography imaging system according to a second embodiment of the present description.

FIG. 4 illustrates another embodiment of an OCT imaging system similar to that shown in FIG. 2A, but in which the reflecting element comprises a small mirror 152 that is inclined with respect to the optical axis of the objective 112 in order to deflect, toward the common channel, incident light waves generated by the light source 111. The mirror 152 is arranged in an image focal plane of the objective 112. The dimensions of the mirror 152 are sufficiently small to not block all of the waves directed into the detection channel. In practice, the mirror 152 is dimensioned to meet the same constraints as those described for the aperture of the apertured mirror 151. Thus, a maximum dimension of the mirror may, according to one example, be smaller than or substantially equal to a maximum dimension of the geometric extent of the image of the source in the plane of the mirror.

In this example embodiment, as is shown in FIG. 4, the illumination channel 101 comprises an optical system 113 for conveying the image of the source 111 to the image focal plane of the objective 112.

In the example of FIG. 4, the reflecting device 134 is a reflective diffraction grating; of course, a similar OCT imaging system could be obtained by replacing the reflective diffraction grating with an inclined mirror, as was described above.

In the example of the OCT imaging systems shown in FIGS. 2A, 2B and 4, the interferometer is a Michelson interferometer and comprises an objective 112 that is arranged upstream of the splitting element 130. Of course, other types of interferometers may be envisioned for OCT imaging systems according to the present description, and in particular Linnik interferometers.

Figure 5:
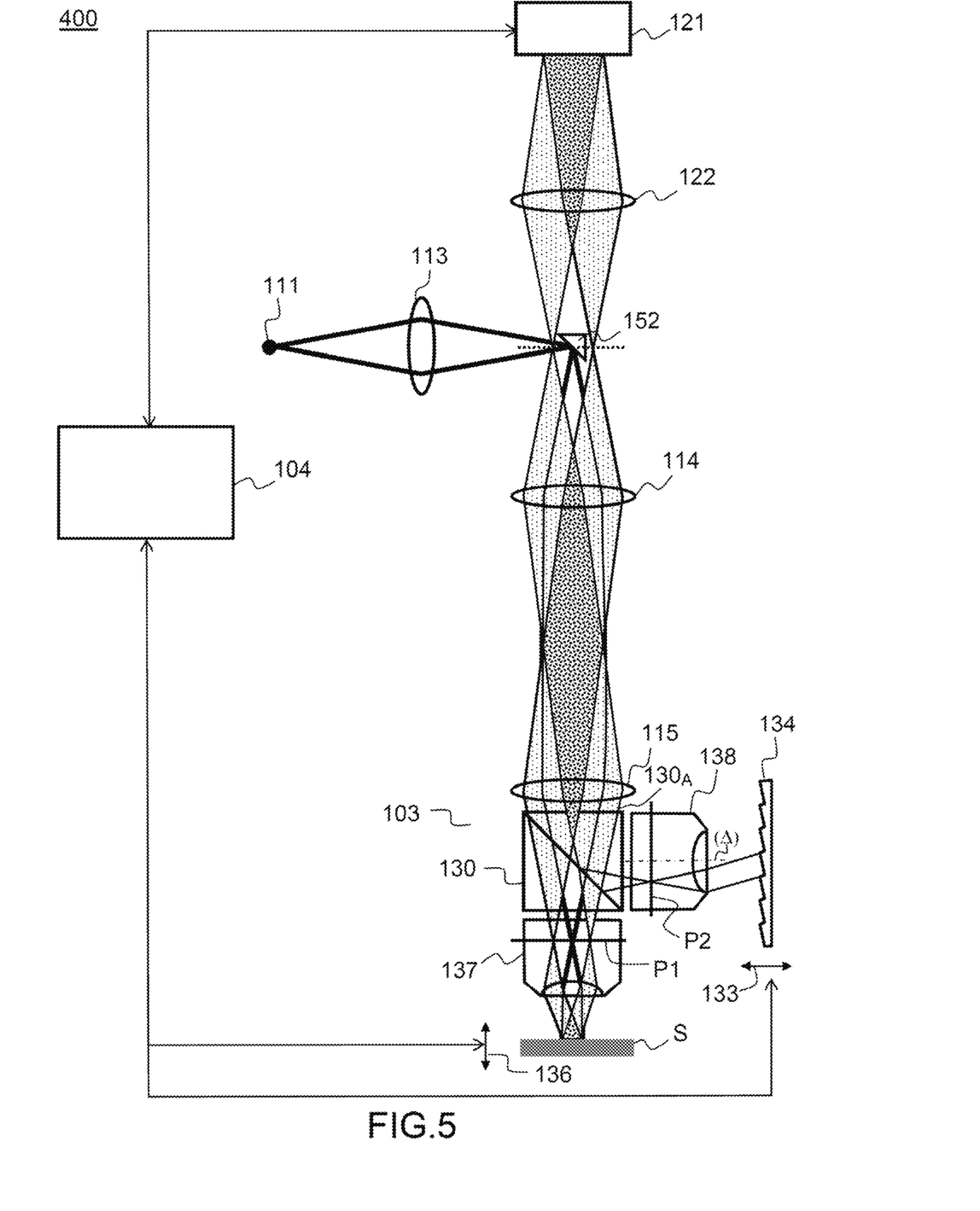

Thus, FIG. 5 shows an example of an OCT imaging system that is substantially similar to the one shown in FIG. 4, but that comprises a Linnik interferometer.

The interferometer 103 then comprises a first objective 138 in the reference arm of the interferometer, and a second objective 137 in the object arm of the interferometer.

These elements may all be dimensioned in the same way as in the preceding examples (FIGS. 2A, 2B and 4), but considering the first objective 138 instead of the objective 112.

In the example illustrated in FIG. 5, the channel common to the illumination channel 101 and the detection channel 102 furthermore comprises an optical relay 114, 115 allowing the reflecting element, in this example the mirror 152, to be conjugated with the image focal plane of the first objective 138.

As may be seen in FIG. 5, in this example, the object arm receives the incident light waves transmitted by the splitting element 130, the transmission coefficient of the splitting element 130 being strictly higher than its reflection coefficient; but the object arm could, in another example, receive the incident light waves reflected by the splitting element 130 in the case where the reflection coefficient of the splitting element 130 is strictly higher than its transmission coefficient.

In the examples illustrated above, the shown splitting element 130 is a cube beamsplitter. Of course, any device suitable for splitting the incident optical power into unequal proportions may be used. For example, the splitting element 130 is a cube beamsplitter consisting of two prisms, a pellicle beamsplitter or a diffraction grating etched into a glass plate.

The present description also relates to full-field OCT methods for imaging a sample S by means of an OCT imaging system according to the present description, for example an OCT imaging system according to one of the embodiments described above.

The OCT imaging method firstly comprises placing a sample S in the object arm of the interferometer 103. The placement of the sample S depends on the sought-after application. For example, the sample may be a zone of the skin of a human being, for example the skin of a finger when acquiring fingerprints from the surface of or from more deeply within the finger, in which case the finger will possibly be pressed against a transparent window, referenced 131 in the figures. In the case of an application to diagnosis of the skin, the size of the window will be decreased to a minimum, for example to a circle of 5 to 10 mm diameter, and the window will be placed at one end of a tube in order to make it easy to access various zones of the human body (face, armpits). It will be noted that since the device is compact and light, it can easily be placed at the end of an articulated arm.

In the case of an application to the detection of defects on semiconductor surfaces, a large flat area will in contrast be necessary in order to allow the surfaces to be placed thereon.

The OCT imaging method according to the present invention comprises producing, by means of the interferometer 103, for each point of the desired imaging field, interference between a reference wave obtained by reflection of incident light waves from the reflecting device of the reference arm of the interferometer, said elementary surface corresponding to said point of the imaging field, and an object wave obtained by backscatter of the incident wave by a voxel of a slice of the sample located at a given depth, said voxel corresponding to said point of the imaging field. There is thus acquired, for at least one value of the optical path difference between the object arm and the reference arm, at least one two-dimensional interferometric signal resulting from the interference for each point of the imaging field, an image of the sample then being calculated from said two-dimensional interferometric signals.

More precisely, when the light source 111 has a small temporal coherence length, interference between the light reflected by the reflecting surface (134, 135) (reference wave) and the light backscattered by the sample S occurs only when the optical paths in the two arms are equal, to within the coherence length. Thus, interference occurs between the reference wave and the light backscattered by each voxel of a slice located in a plane perpendicular to the optical axis of the object arm, at a given depth in the sample, which depth is called the coherence slice, a voxel being an elementary volume defined in the coherence slice. The light backscattered by each voxel is representative of the amplitude of the coherent sum of the waves backscattered by all of the elementary scattering structures present in this voxel.

The interferometric signals resulting from the optical interference between the reference waves and the waves backscattered by the various voxels are acquired in parallel at a time t by the acquiring device 121. An interferometric image S corresponding to the interference state at a given time t of the coherence slice results. An interferometric image pixel or image element located at a given position (x, y) defined relative to a two-dimensional coordinate system associated with the acquiring device 121, has a value S(x,y,t) that corresponds to the intensity of the interferometric signal that was acquired at the time t and for the position (x, y), and that resulted from the interference between the wave backscattered by the voxel of corresponding position in the sample and the reference wave reflected by an elementary area of the reflecting surface of the reference arm of corresponding position.

The processing unit 104 is configured to generate an image of the sample S from at least one two-dimensional interferometric signal obtained by the acquiring device 121.

Various known prior-art methods allow for an image of the sample to be calculated. For example, a method involving modulation with 4 phases is described in the article "*Full-field optical coherence tomography*" by A. Dubois and C. Boccara, extracted from the work "*Optical Coherence Tomography—Technology and Applications*"—Wolfgang Drexler—James G. Fujimoto—Editors—Springer 2009. In this method, interference signals are acquired by the acquiring device for 4 phase-shift values and the image of the sample is reconstructed by calculating the square root of $(I_0-I_{180})^2+(I_{90}-I_{270})^2$, where $I_0$, $I_{90}$, $I_{180}$, $I_{270}$ are the interference signals acquired for these 4 phase-shift values.

Figure 6:
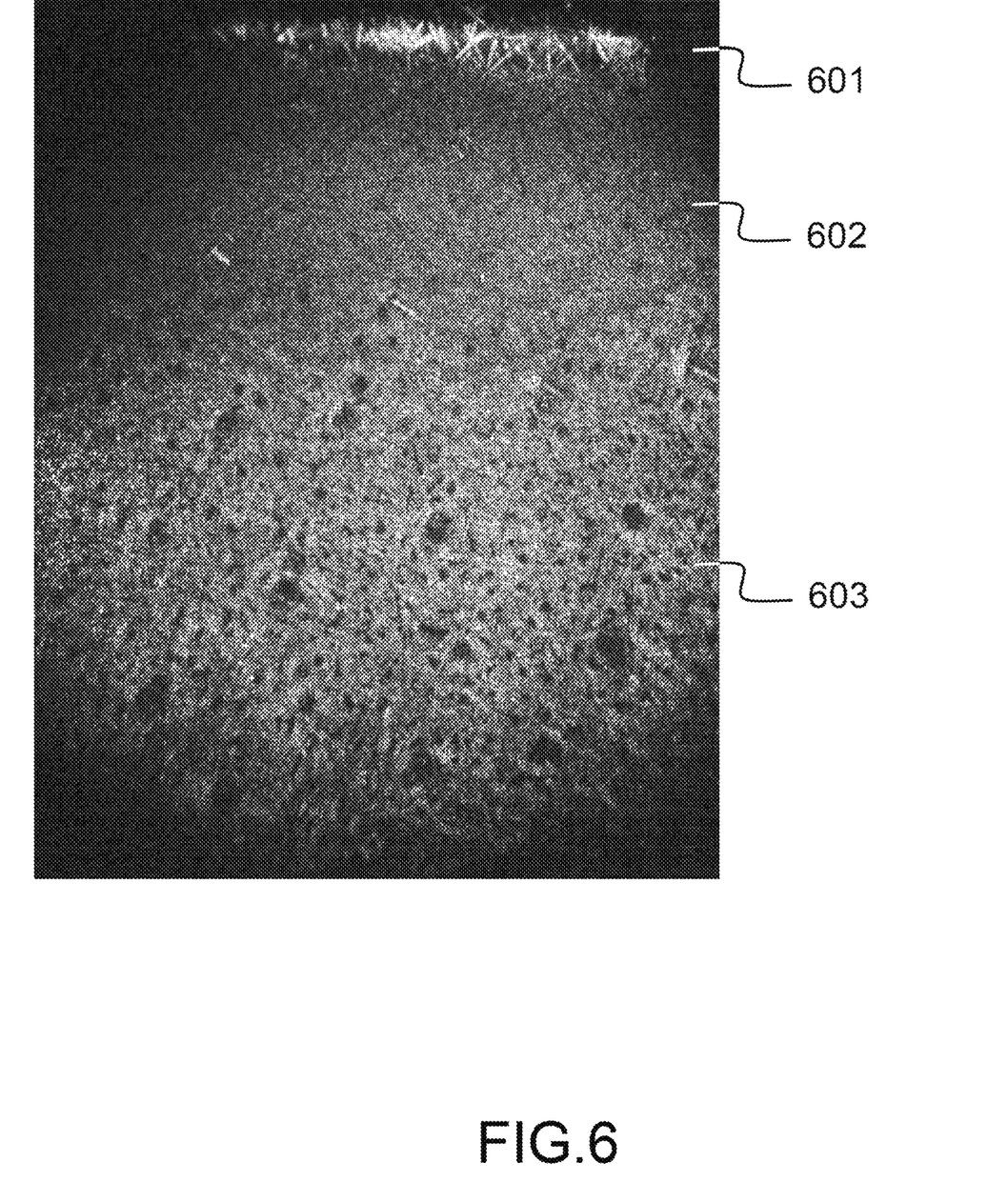
FIG. 6 shows an experimental image of a cross section of a skin element obtained in vivo by means of a full-field optical-coherence-tomography imaging system such as shown in FIG. 2B.

FIG. 6 shows an experimental image of a sample of skin, imaged at depth therein, and obtained by a full-field OCT imaging system according to the present description, and more precisely a full-field OCT imaging system such as shown in FIG. 2B.

The system comprises a source 111 formed from an LED that emits incoherent light at a wavelength of 850 nm (LED M850L3, Thorlabs®), with a spectral width of 30 nm. The system comprises a Michelson interferometer 103 and a CMOS camera 121 (Adimec® CXP) that is able to take up to 700 images per second. The geometric extent of the light source is enlarged by a factor of 4 by means of a pair of lenses (not shown in FIG. 2B) in order to decrease the divergence of the light emerging from the LED, so that most of the emitted light is emitted into the acceptance angle of the objective 112. The LED is focused onto the aperture of the mirror 131, which is circular and of 4 mm diameter. A reflecting device formed of an inclined mirror 135 is used, the angle of inclination being 1.15°, so that the reflected light is reflected by the mirror 151 toward the detection channel 102. A piezoelectric element 133 is used to modulate the interference pattern detected by the camera. Images are acquired for 4 phase-shift values and the image of the sample is reconstructed by calculating the square root of $(I_0-I_{180})^2+(I_{90}-I_{270})^2$, where $I_0$, $I_{90}$, $I_{180}$, $I_{270}$ are the interference signals acquired for these 4 phase-shift values.

In FIG. 6, a zone 601 on the surface of the skin, a zone 602 below the surface of the skin and a zone 603 located at depth under the skin may be seen.

In this example, the use of an inclined mirror 135 makes it possible to obtain, with a single image (without axial movement of the sample or of the reference mirror, with the exception of the piezoelectric movement used to modulate the phase) information from deep within the sample. Thus, it is possible to estimate that the zone 601 is at a depth of 44 μm, that the zone 602 is at a depth of 123 μm and that the zone 603 is at a depth of 312 μm. The intensity difference is related to damping of ballistic light by the biological tissue.

The OCT imaging methods and systems described above are in particular applicable to the acquisition of fingerprints or to imaging of the skin. They may also be applied generally in any situation in which the photon budget is limited. They are furthermore applicable to any samples, whether they be biological or not.

The invention claimed is:

1. A full-field optical-coherence-tomography system for imaging a sample, comprising:
   an illumination channel comprising a light source for emitting incident light waves;
   an interferometer comprising:
      at least one first objective, the light source being arranged in an image focal plane of the first objective or in a plane conjugate with an image focal plane of the first objective; and
      a splitting element suitable for receiving, via an entrance face, the incident light waves and suitable for forming an object arm intended to receive the sample and a reference arm in which is arranged a reflecting device; and wherein the splitting element has a reflection coefficient and a transmission coefficient that are not equal, such that the proportion of the optical power of the incident light waves sent to the object arm is strictly higher than the proportion of the optical power of the light waves sent to the reference arm;
      the reflecting device is suitable for directing the reflected incident light waves in a direction that is different from the direction of incidence, that is to say along an optical path making an angle α with an incident optical path, and
      the interferometer is suitable for producing, when the sample is placed in the object arm of the interferometer, at each point of an imaging field, interference between a reference wave obtained by reflection of incident light waves from an elementary surface of the reflecting device corresponding to said point of the imaging field and an object wave obtained by backscatter of incident light waves by a voxel of a slice of the sample at a given depth, said voxel corresponding to said point of the imaging field, angle α allowing angular spatial separation between the incident light wave and the reference wave;
   a detection channel comprising a device for acquiring two-dimensional images, and wherein the device for acquiring two-dimensional images is positioned in a conjugate plane of the reflecting device and suitable for acquiring two-dimensional interferometric signals resulting from the interference produced at each point of the imaging field;
   the illumination channel and the detection channel comprise a common channel at least between said entrance face of the splitting element and a reflecting element, said reflecting element separating the illumination channel and the detection channel and being positioned in an image focal plane of said first objective, or in a conjugate plane of said image focal plane of the first objective, said reflecting element comprising a mirror that is inclined with respect to an optical axis of the first objective, and whose shape and dimensions are suitable, in combination with said angular spatial separation, for letting pass, in the detection channel, at least one portion of the light waves directed by the reflecting device of the reference arm and for letting pass, in the illumination channel, at least one portion of the incident light waves;
   a processing unit configured to calculate an image of the sample from said two-dimensional interferometric signals.

2. The imaging system as claimed in claim 1, wherein the reflection coefficient and the transmission coefficient of the splitting element are such that at least 90% of the optical power of the light waves incident on the splitting element are sent toward the object arm.

3. The imaging system as claimed in claim 1, wherein the reflecting element comprises a mirror that is inclined with respect to the optical axis of the first objective, and which is apertured for the passage of the incident light waves, the dimensions of the aperture being sufficiently small to not block all of the light waves directed into the detection channel.

4. The imaging system as claimed in claim 1, wherein the reflecting element comprises a mirror that is inclined with respect to the optical axis of the first objective in order to deflect toward the common channel the incident light waves, and that has dimensions that are sufficiently small to not block all of the waves directed into the detection channel.

5. The imaging system as claimed in claim 1, wherein the reflecting device comprises a reflective diffraction grating, for example a blazed grating.

6. The imaging system as claimed in claim 1, wherein the reflecting device comprises an inclined mirror.

7. The imaging system as claimed in claim 1, wherein the interferometer is a Michelson interferometer, said first objective being arranged in the common channel of the illumination and detection channels.

8. The imaging system as claimed in claim 1, wherein the interferometer is a Linnik interferometer and comprises said first objective in the reference arm of the interferometer, and a second objective in the object arm of the interferometer.

9. The imaging system as claimed in claim 8, wherein said objectives are microscope objectives.

10. A full-field optical-coherence-tomography method for imaging a sample by means of an imaging system as claimed in claim 1, comprising:
    placing the sample in the object arm of the interferometer;
    producing, by means of said interferometer, for each point of an imaging field, interference between a reference wave obtained by reflection of incident light waves from the reflecting device of the reference arm of the interferometer, said elementary surface corresponding to said point of the imaging field, and an object wave obtained by backscatter of the incident wave by a voxel of a slice of the sample at a given depth, said voxel corresponding to said point of the imaging field;
    acquiring, for at least one value of the optical path difference between the object arm and the reference arm, at least one two-dimensional interferometric signal resulting from interference for each point of the imaging field;
    calculating an image of the sample from said two-dimensional interferometric signals.

* * * * *